(12) United States Patent
Düring

(10) Patent No.: US 6,515,106 B1
(45) Date of Patent: Feb. 4, 2003

(54) LYSOZYME-ANALOGOUS POLYPEPTIDES WITH AN ANTI-MICROBIAL EFFECT, THEIR PRODUCTION AND USE

(75) Inventor: Klaus Düring, Frechen (DE)

(73) Assignee: MPB Cologne GmbH Molecular Plant and Protein Biotechnology, Cologne (DE)

( * ) Notice: Subject to any disclaimer, the term of this patent is extended or adjusted under 35 U.S.C. 154(b) by 0 days.

(21) Appl. No.: 09/567,563

(22) Filed: May 5, 2000

Related U.S. Application Data

(63) Continuation of application No. PCT/DE98/03287, filed on Oct. 31, 1998.

(30) Foreign Application Priority Data

Nov. 5, 1997 (DE) .......................................... 197 49 973

(51) Int. Cl.[7] .......................... C07K 1/00; C07H 21/02; C07H 21/04; C12N 9/36; C12N 15/00
(52) U.S. Cl. ...................... 530/350; 435/206; 435/440; 536/23.2; 536/23.1
(58) Field of Search ................................ 435/206, 440; 530/350, 35; 576/23.1, 23.2

(56) References Cited

PUBLICATIONS

Rennell et al. Systematic mutation of bacteriophage T4 lysozyme. Journal of Molecular Biology. (1991) vol. 222, pp. 67–88.*

"Antimicrobial effects of lysozyme against gram–negative bacteria due to covalent binding of palmitic acid." Ibrahim, Hishram Radwan; Kato, Akio; Kobayashi, Kunihiko, Fac. Agric. Yamagucki Univ. (Chemical abstract).

* cited by examiner

*Primary Examiner*—Ponnathapu Achutamurthy
*Assistant Examiner*—Yong Pak
(74) *Attorney, Agent, or Firm*—Marianne Fuierer; Yongzhi Yang; Steven J. Hultquist

(57) ABSTRACT

The present invention relates to polypeptides exhibiting antibiotic, and anti-viral and anti-cancer effects. In particular, the invention relates to modified T4 lysozyme, polypeptides comprising fragments of T4 lysozyme and to the production and use thereof. The fields of application for this invention are wide-ranging, and include, for example, human and veterinary uses, resistance cultivation in plants and prevention of bacterial and/or fungal-mediated food spoilage.

10 Claims, No Drawings

US 6,515,106 B1

LYSOZYME-ANALOGOUS POLYPEPTIDES WITH AN ANTI-MICROBIAL EFFECT, THEIR PRODUCTION AND USE

CROSS-REFERENCE TO RELATED APPLICATIONS

This application is filed under the provisions of 35 USC §111 and is a continuation of International Patent Application No. PCT/DE98/03287 filed Oct. 31, 1998, which claims priority of German Patent Application No. 197 49 973.2 filed Nov. 5, 1997.

FIELD OF THE INVENTION

The present invention relates to polypeptides exhibiting antibiotic, and anti-viral and anti-cancer effects. In particular, the invention relates to modified T4 lysozyme, polypeptides comprising fragments of T4 lysozyme and to the production and use thereof. The fields of application for this invention are wide-ranging, and include, for example, human and veterinary uses, resistance cultivation in plants and prevention of bacterial and/or fungal-mediated food spoilage.

BACKGROUND OF THE INVENTION

T4 lysozyme is a protein which is formed from bacteriophage T4. T4 lysozyme functions to open the bacterial host cell after it has been propagated therein, and to allow it to enter the environment. It has been assumed that the enzyme activity (muramidase) of T4 lysozyme destroys the bacteria (Tsugita, A. (1971) Phage lysozyme and other lytic enzymes; in: Boyer, P. D. (ed.) The Enzymes, Vol. V. Academic Press, New York, p. 344–411). T4 lysozyme is known to effect a specific cleavage between C-1 of the muramic acid group and C-4 of acetylglucosamine. This cleavage ruptures the bacterial muramine network ruptures and destabilizes the cell wall. However, the lysozyme must first traverse the bacterial cell membrane to access its substrate, the muramine layer. Until now it has not been possible to explain the transport route of the T4 lysozyme through the inner cell membrane to the muramine layer. It has been assumed that, as a consequence of rupture of the muramine layer the bacteria burst open through destabilization and are thus destroyed.

Further enzymatic or other biochemical functions, e.g. membrane affinities, of the T4 lysozyme have not previously been described.

DE 39 26 390 describes the introduction of lysozyme genes as exogenic or additional DNA into plants, to increase resistance to fungi and animal microbes.

Lysozyme genes are understood here to be any nucleic acids (e.g., DNA) that encode lysozymes. Lysozymes protect the transformed plants against plant-pathogenic fungi and animal microbes.

The nucleic acid used to transform plants preferably includes a promotor active in plants, a chimeric gene for T4 lysozyme, containing the coding DNA sequences for the signal peptide of alpha-amylase from barley and for the lysozyme of the bacteriophage T4, and a polyadenylation signal. The amino acid sequence of the T4 lysozyme is obtained from the phage T4.

Through a consensus sequence for the N-bound glycosylation (Asn-X-Ser/Thr) existing in the amino acids 140–142, a glycosylated form of the T4 lysozyme protein is produced in plants (Düring, K.; Porsch, P.; Fladung, M.; Lörz, H.; Transgenetic potato plants resistant to the phytopathogenic bacteria *Erwina carotovora*; The Plant Journal 3, 587–598 (1993) ). The glycosylation occurring in planta, which has not been described in patent DE 39 26 390, can be the cause of a change in the enzyme properties or functionality. It is possible, for example, that the conversion rate of the enzyme is significantly reduced.

DE 39 26 390 describes only the utilization of lysozymes for increasing the resistance of transgenic plants, containing a lysozyme-coding DNA sequence, to fungi and animal microbes. The described gene constructions are limited by the aforementioned problems. Moreover, these gene constructions do not solve the problem of potential influencing factors, which can reduce the efficiency of the described system in transgenic plants. Production of the T4 lysozyme in transgenic plants, and use of T4 lysozyme as a medical remedy in human or veterinary medicine, or as a preservative additive is not considered.

The mode of action of the T4 lysozyme (for which at the time of registration of patent DE 39 26 390 only the muramidase activity was known) on fungi and other microbes has still not been explained. The definition of lysozyme genes given in patent DE 39 26 390 relates only to translation into proteins which possess the known properties of lysozymes.

There is a need in the art for new types of polypeptides with a wide range of useful properties, such as antibiotic, anti-viral and anti-cancer properties.

SUMMARY OF THE INVENTION

The invention generally relates to antibiotic polypeptides comprising a modified T4 lysozyme, or a functional equivalent thereof, which exhibits antibiotic activity without exhibiting muramidase activity. The polypeptide preferably does not comprise full-length, native T4 lysozyme.

In a preferred aspect, the native glutamic acid residue at position 11 of the T4 lysozyme is replaced by any amino acid residue other than glutamic acid.

In another preferred aspect, the segment is selected from the group consisting of the amino acid sequence of SEQ ID NO: 1, and fragments and derivatives thereof, wherein X is any amino acid residue except glutamic acid.

A preferred set of segments includes:
  amino acids 12–164 of SEQ ID NO: 1, and subsegments and functional equivalents thereof;
  amino acids 126–141 of SEQ ID NO: 1, and subsegments and functional equivalents thereof;
  amino acids 143–155 of SEQ ID NO: 1, and subsegments and functional equivalents thereof;
  amino acids 74–164 of SEQ ID NO: 1, and subsegments and functional equivalents thereof;
  amino acids 114–164 of SEQ ID NO: 1, and subsegments and functional equivalents thereof; and
  amino acids 124–164 of SEQ ID NO: 1, and subsegments and functional equivalents thereof.

Another preferred group of functional equivalents includes:
  amino acids 12–164 of SEQ ID NO: 1 comprising one or more mutations at any one or more of positions 140–142, which mutation(s) do not eliminate the antibiotic activity of the polypeptide.
  amino acids 126–141 of SEQ ID NO: 1 comprising one or more mutations at any one or more of position s 140–141, which mutation(s) do not eliminate the antibiotic activity of the polypeptide.

amino acids 74–164 of SEQ ID NO: 1 comprising one or more mutations at any one or more of positions 140–142, which mutation(s) do not eliminate the antibiotic activity of the polypeptide.

amino acids 114–164 of SEQ ID NO: 1 comprising one or more mutations at any one or more of positions 140–142, which mutation(s) do not eliminate the antibiotic activity of the polypeptide.

The antibiotic polypeptide may also consist of the above-listed sets of segments, subsegments and functional equivalents.

The invention also relates methods for producing the segments, subsegments and functional equivalents (e.g., proteolysis of the native protein, chemical synthesis, recombinant production).

In another aspect, the invention relates to a nucleic acid encoding a polypeptide comprising a segment of T4 lysozyme, or a functional equivalent of said segment, which polypeptide exhibits antibiotic activity but which does not exhibit muramidase activity. The recombinant nucleic acid preferably does not encode full-length T4 lysozyme.

The invention also relates to a method for killing a microbe and/or controlling a population of microbes. The method generally comprises bringing the microbe and/or population of microbes into contact with a polypeptide comprising a segment of T4 lysozyme, or comprising a functional equivalent of said segment, which polypeptide exhibits antibiotic activity but which does not exhibit muramidase activity. In one aspect, the method is used to kill a bacteria or fungus, or to eliminate or control a bacterial colony or a fungal colony. In another aspect, the microbe is a pathogen of an organism and the organism is genetically modified to produce the polypeptide, thereby bringing the pathogenic organism and/or colony into contact with the polypeptide, to effect its antibiotic effect on the organism or colony. In a preferred aspect, the microbe is a plant pathogen and the polypeptide is applied to the plant and/or the plant is genetically modified to produce the polypeptide.

The invention provides microbe control compositions comprising antibiotic polypeptides formulated for application to the target microbes or their situs.

Antibiotic compositions of the invention generally contain one or more of the antibiotic polypeptides described above and a carrier acceptable for the specific use for which the composition is intended. The invention includes methods of killing or controlling microbes which involve applying such antibiotic compositions to the microbes or their environment. In one aspect, the antibiotic compositions of the present invention are administered in the form of a spray or a time release dosage unit. The antibiotic compositions can also comprise various other known antibiotic polypeptides targeting the same or different microbes.

Methods of making antibiotic compositions are also included within the scope of the present invention. These methods generally comprise bringing one or more of the antibiotic polypeptides into association with a suitable carrier, diluent or excipient therefor.

Definitions

As used herein, the term "antibiotic" is broadly used to refer to the capacity to kill or injure cells, and specifically includes anti-bacterial, anti-fungal, anti-microbial, anti-viral and anti-cancer effects.

As used herein, the term "antibiotically effective" and the like, is used to indicate an amount or concentration of an antibiotic compound which is sufficient to reduce the number of target cells in a target locus (e.g., a container of food, an infected site on an organism, or an entire organism in the case of a systemic infection), as compared to a corresponding locus in the absence of the amount or concentration of the antibiotic polypeptide.

The word "transform" is broadly used herein to refer to introduction of an exogenous polynucleotide sequence into a prokaryotic or eukaryotic cell by any means known in the art (including, for example, direct transmission of a polynucleotide sequence from a cell or virus particle as well as transmission by infective virus particles and transmission by any other known means for introducing a polynucleotide into a cell), resulting in a permanent or temporary alteration of genotype and in an immortal or non-immortal cell or cell line.

The term "polypeptide" is used herein to broadly refer to amino acid sequences of any length, including peptides and proteins.

As used herein, the terms "functionally equivalent," "functional equivalent" and the like, in reference to polypeptides, refer to fragments, analogs, derivatives and the like, which retain some or all of the antibiotic activity as the exemplified peptides.

As used herein, the terms "variants" or "variations" of genes or other nucleic acid sequences refer to nucleotide sequences which encode the same peptides or which encode functionally equivalent polypeptides.

DETAILED DESCRIPTION OF THE INVENTION

The inventors have surprisingly discovered, by structural-functional analysis of the T4 lysozyme molecule, that the antibiotic effect of the T4 lysozyme is independent of the enzymatic muramidase activity. It was found that on heating the denatured T4 lysozyme, it no longer possessed any enzyme activity, but still exhibited the full antibiotic effect.

Furthermore, an amphipathic alpha-helix was identified in the terminal-C part of the T4 lysozyme, which surprisingly is sufficient on its own to exert an antibiotic effect. However, this peptide sequence (amino acid 143–155 in the T4 lysoyzme) retains none of the native enzymatic activity. The antibiotic effect of lysozymes can be effected by a membrane-interacting function, from the T4 lysozyme, for example, by the amphipathic alpha-helix 143–155.

Contrary to the previously known properties of the T4 lysozyme, no enzymatically active protein is required to provide the antibiotic effect.

According to the invention, polypeptides have been prepared which, although derived from lysozymes, in particular the T4 lysozyme, no longer contain the lysozyme muramidase activity.

In a preferred variant according to the invention, the compounds of the invention comprise the following sequence (SEQ ID NO: 1):

| MNIFEMLRID | XRLRLKIYKD | TEGYYTIGIG | HLLTKSPSLN | AAKSELDKAI | 50 |
| GRNCNGVITK | DEAEKLFNQD | VDAAVRGILR | NAKLKPVYDS | LDAVRRCALI | 100 |

```
NMVFQMGETG  VAGFTNSLRM  LQQKRWDEAA  VNLAKSRWYN  QTPNRAKRVI  150
TTFRTGTWDA  YKNL                                            164
``` in which X represents any amino acid except glutamic acid. The compounds preferably do not comprise the full-length native sequence of T4 lysozyme.

The polypeptide of SEQ ID NO: 1, segments of this polypeptide, as well as polypeptides which have been derived from SEQ ID NO: 1 or its active subsegments by mutation or fragmentation are included as aspects of the invention.

A particularly preferred variant of SEQ ID NO: 1 comprises one or more mutations of the consensus sequence NQT (amino acids 140 to 142 in the T4 lysozyme). Mutation (s) at these positions prevent N-bound glycosylation transgenic eukaryotes. N-bound glycosylation of the polypeptide can reduce the antibiotic activity.

Preferred segments of SEQ ID NO: 1 include the amino acids 12–164 of the T4 lysozyme and subsegments thereof which exhibit some or all of the antibiotic activity of the polypeptide of SEQ ID NO: 1.

The invention also relates to segments of SEQ ID NO: 1, and to polypeptides which comprise such segments. Preferred examples include:

amino acids 126–141 WDEAAVNLAKSRWYNQO, optionally comprising one or more mutations at positions 140 and/or 141;
   amino acids 143–155 PNRAKRVIFTFRT;
   amino acids 126–141 WDEAAVNLAKSRWYNQ, optionally comprising one or more mutations at positions 140 and/or 141; and
   amino acids 143–155 PNRAKRVIFTFRT.

In a preferred aspect the invention provides recombinant proteins, comprising at least amino acids 126–141 and/or 143–155 (amphipathic helix) of the T4 lysozyme. The invention may also comprise partially homologous sequences with the same functionality, which have been formed through amino acid exchanges and/or as a component fused onto other amino acid sequences.

A further aspect of the present invention relates to addition salts, complexes, or prodrugs such as esters of the antibiotic polypeptides, especially the pharmaceutically or agriculturally acceptable acid addition salts. The acid addition salts can be prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. Esterification to form derivatives such as the methyl or ethyl esters can be prepared by standard procedures.

The N-terminus and C-terminus of the polypeptides can be blocked to further inhibit proteolysis by metabolic enzymes. Derivation of peptides to block the N-terminus or C-terminus is known in the art. For example, the N-terminus can be acetylated by methods known to those of ordinary skill in the art; the C-terminus can be amidated as is well known in the art.

The polypeptides may also be derivatized using various polymers known in the art to stabilize, solublize and/or facilitate transport of the polypeptides across biological membranes.

In a preferred embodiment of the invention, the antibiotic polypeptides may be presented as fusion polypeptides, the amino acid sequence of which includes one or more antibiotic polypeptides of the present invention. In various specific embodiments, two or more of the antibiotic polypeptides are linked, for example, by peptide bonds between the N-terminus of one portion and the C-terminus of another portion. In other aspects, one or more of the antibiotic polypeptides can be linked to one or more heterologous peptides or proteins to form antibiotic fusion peptides. Molecules comprising such portions linked by hydrocarbon linkages are also provided. Derivatives of the foregoing fusion proteins are also provided (e.g., branched, cyclized, N- or C-terminal chemically modified, etc.).

Analogs which have one or more amino acid substitutions forming a branched polypeptide (e.g., by substitution with an amino acid or amino acid analog having a free amino- or carboxy-side chain that forms a polypeptide bond with a sequence of one or more amino acids, including but not limited to prolines) or allowing circularization of the polypeptide (e.g., by substitution with a cysteine, or insertion of a cysteine at the amino- or carboxy-terminus or internally, to provide a sulfhydryl group for disulfide bond formation), are also provided.

Nonclassical amino acids or chemical amino acid analogs can be introduced as a substitution, added at a terminus or inserted between existing amino acid residues of the antibiotic polypeptides of the present invention. Non-classical amino acids include but are not limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogs in general.

Furthermore, the antibiotic polypeptide may comprise D (dextrorotary) or L (levorotary) amino acid residues. The presence of D-conformation amino acids can inhibit the ability of proteases to degrade the antibiotic polypeptides of the present invention.

The antibiotic polypeptide derivatives include peptides containing, as a primary amino acid sequence, all or part of the particular antibiotic polypeptide sequence including altered sequences in which functionally equivalent amino acid residues are substituted for residues within the sequence resulting in a polypeptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such antibiotic polypeptide derivatives can be made either by chemical synthesis or by recombinant production from a nucleic acid encoding the antibiotic polypeptide.

Preparation of the Antibiotic Polypeptides of the Invention

The mutated polypeptides can be obtained by amino acid exchange of the lysozyme extracted from natural sources. In a preferred aspect, the compounds of the invention comprise a mutation at position 11, replacing the glutamic acid residue with another amino acid. This mutation can readily be accomplished using standard protein-technical operations. Examples include cloning of sub-fragments, polymerase chain reaction-amplification and modification and site-directed mutagenesis of certain sections of the DNA in the native state or simultaneous introduction of modifications.

In a preferred aspect, the T4 lysozyme is extracted from a natural source, and fragments are produced by cleavage with proteases of the extracted T4 lysozyme.

The polypeptides of the invention may also be chemically synthesized. A preferred technique is the Merrifield process. See Merrifield (1963) J. Amer. Chem. Soc. 85:2149–2154 and Merrifield (1965) Science 150:178–185. This procedure, using many of the same chemical reactions and blocking groups of classical peptide synthesis, provides a growing polypeptide chain anchored by its carboxyl terminus to a solid support, usually cross-linked polystyrene or styrenedivinylbenzene copolymer. This method conveniently simplifies the number of procedural manipulations, since removal of the excess reagents at each step is effected simply by washing the polymer.

The antibiotic polypeptides can also be synthesized using a peptide synthesizer. The composition of the synthetic polypeptides may be confirmed by amino acid analysis or sequencing, e.g., see the Edman degradation procedure; see also Creighton, 1983, Proteins, Structures and Molecular Principles, W. H. Freeman and Co., N.Y., pp. 34–49.

In a particularly preferred embodiment, the polypeptides of the invention are produced by recombinant techniques, using well-known molecular biology procedures. See S. L. Beaucage and M. H. Caruthers (1981), Tetrahedran Lett. 22:1859. For example, such methods are useful for the production of partial sequences or for insertion of specific or random mutations in the coding DNA sequences. Polynucleotides encoding the antibiotic polypeptides of the invention can be synthesized readily and are a further aspect of the present invention. These polynucleootides can be used to genetically engineer, prokaryotic or eukaryotic cells for production of the antibiotic polypeptides. Examples of suitable cells include bacteria, insect cells, viruses, plant cells, fungi, algae, yeast, mammalian, etc. The antibiotic polypeptides preferably exhibit the antibiotic effects, but preferably do not exhibit the muramidase activity, of native T4 lysozyme. Additionally, organisms can be transformed to express these recombinant nucleic acids and to thereby effect a direct antibiotic effect in vivo.

If desired, the polynucleotide of the present invention can be amplified using PCR. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of Globin Genomic Sequences and Restriction Site Analysis for Diagnosis of Sickle Cell Anemia," Science 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus,* the amplification process can be completely automated. Other enzymes which can be used are known to those skilled in the art.

The various methods employed in the preparation of plasmids and transformation of host organisms are well known in the art and are described, for example, in U.S. Pat. Nos. 5,011,909 and 5,130,253. These patents are incorporated herein by reference. These procedures are also described in Maniatis, T., E. F. Fritsch, J. Sambrook (1982) Molecular Cloning: A Laboratory Manual, Cold Spring Harbor Laboratory, New York. Thus, it is within the skill of those in the genetic engineering art to extract DNA from microbial cells, perform restrictions and enzyme digestions, electrophorese DNA fragments, tail and anneal plasmid and insert DNA, ligate DNA, transform cells (e.g., *E. coli,* or plant cells, fungal cells, algae cells, eukaryotic cells, etc.), prepare plasmid DNA, electrophorese proteins, and sequence DNA.

In one aspect the present invention is directed to a cell transformed with a polynucleotide encoding a polypeptide comprising an antibiotic polypeptide of the invention or a functional equivalent of an antibiotic polypeptide of the invention.

Hosts which may be employed according to techniques well known in the art for the production of the polypeptides of the present invention include unicellular microorganisms such as prokaryotes, i.e., bacteria; and eukaryotes such as fungi, including yeasts, algae, protozoa, molds, and the like, as well as plant cells, both in culture or in planta, and animal cells and viruses. It is preferred that the host is one which is not destroyed by the antibiotic effect of the polypeptide being produced. Examples of suitable bacteria susceptible to transformation by the polynucleotides of the invention include members of the Enterobacteriaceae, such as strains of *Escherichia coli;* Salmonella; Bacillaceae, such as *Bacillus subtilis;* Pseudomonas; Pneumococcus; Streptococcus; *Haemophilus influenzae,* and yeasts such as Saccharomyces, among others.

The polynucleotide sequences of the present invention can be introduced directly into the genome of the transformable host cell or can first be incorporated into a vector which is then introduced into the host. Exemplary methods of incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids, and phages.

It is well known in the art that when synthesizing a gene for improved expression in a host cell it is desirable to design the gene such that its frequency of codon usage approaches the frequency of preferred codon usage of the host cell. For purposes of the present invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell.

Thus, in one embodiment of the present invention, bacteria, algae, fungi, plants, or other cells can be genetically engineered, e.g., transformed with polynucleotides encoding the subject peptides to attain desired expression levels of the subject peptides. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for the host cell, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed genes in the host cell to specify that amino acid. As is appreciated by those skilled in the art, the distribution frequency of codon usage utilized in the synthetic gene is a determinant of the level of expression.

Assembly of the polynucleotide sequences of this invention can be performed using standard technology known in the art. For example, a gene designed for enhanced expression in a host cell can be assembled within a DNA vector from chemically synthesized oligonucleotide duplex segments. Preferably, the DNA vector or construct has an operable promoter and suitable termination signals. The polynucleotide sequence can then be introduced into a host cell and expressed by means known in the art. Preferably, the polypeptide produced upon expression of the nucleotide sequence is functionally equivalent to the purified polypeptide.

With the teachings provided herein, one skilled in the art can readily produce and use the various polypeptides and polynucleotide sequences described herein.

The polynucleotide sequences and antibiotic polypeptides useful according to the subject invention include not only the exemplified sequences but also fragments of these sequences, variants, mutants, and fusion proteins which retain the characteristic antibiotic activity of the peptides specifically exemplified herein.

The present invention also provides chimeric polypeptides comprising two or more antibiotic polypeptides of the present invention, or one or more polypeptides of the present invention with one or more heterologous polypeptides. The polypeptides which are combined need not themselves be antibiotic so long as the combination of portions creates a chimeric protein which is antibiotic.

Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of the antibiotic polypeptides.

Polynucleotide sequences encoding the antibiotic polypeptides of the present invention can be introduced into a wide variety of plant or animal hosts. Expression of the gene results, directly or indirectly, in the production and maintenance of the antibiotic polypeptide. The result is control or eradication of the pathogenic microbe.

In one embodiment, the gene encoding the antibiotic polypeptide is only expressed or maintained by the transformed host for a relatively short period of time, such as days or weeks, so that the transformed organism does not continue indefinitely to express the antibiotic polypeptide. For example, in microbial hosts the plasmid may be constructed without plasmid maintenance systems or with insufficient plasmid maintenance function to ensure long-term survival of the antibiotic polypeptide-encoding plasmid. Alternatively, various plasmid maintenance systems known in the art can be applied, to ensure long-term survival of the antibiotic polypeptide-producing plasmid.

A wide variety of methods are available for introducing a polynucleotide sequence encoding an antibiotic polypeptide into a microorganism host under conditions which allow for stable maintenance and expression of the gene. These methods are well known to those skilled in the art and include, for example, the methods described in U.S. Pat. No. 5,135,867, which is incorporated herein by reference.

In a preferred aspect of the invention, the polypeptide of SEQ ID NO: 1 serves as a "carrier protein" for other antibiotically active peptides, preferably amphiphatic helices, resulting in the improved stabilization of the antibiotically active peptides. For example, the polypeptide sequence 143–155 (PNRAKRVIFTFRT) can be substituted by another natural polypeptide sequence or one developed by rational design.

Methods for Using the Polypeptides of the Invention

The polypeptides of the invention exhibit some or all of the antibiotic properties of T4 lysozyme. The polypeptides of the invention are preferably at least as effective at killing and/or controlling the growth of microbes as T4 lysozyme, most preferably the polypeptides are more effective than T4 lysozyme. However, it will be appreciated by those of skill in the art that polypeptides which are less potent than T4 lysozyme are also useful. The antibiotic effectiveness of the polypeptides of the invention is illustrated by their effect on survival rates of *Escherichia coli* cells in Table 1.

TABLE 1

Relative survival rates of *Escherichia coli* cells after 1 hr incubation with T4 lys or derived T4 lys in 0.1 × PBS; T4 lys in 0.1 × PBS/1% SMSO; heat denatured T4 lys (10 min 80° C.) in 0.1 × PBS/1% DMSO; M6K T4 lys mutant in 0.1 × PBS; peptide A4 in 0.1 × PBS (all final concentrations)

| T4 lys in 0.1 × PBS | T4 lys in 0.1 × PBS/1% DMSO | Heat denatured T4 lys in 0.1 × PBS/1% DMSO | M6K T4 lys mutant in 0.1 × PBS | Peptide A4 in 0.1 × PBS | |
|---|---|---|---|---|---|
| 10 µg | 10 µg | 10 µg | 1 µg | 10 µg | 1 µg |
| 0.14 +/− 0.09 | 0.09 +/− 0.07 | 0.19 +/− 0.16 | 0.36 +/− 0.18 | 0.05 +/− 0.09 | 0.74 +/− 0.14 |

The table shows the lack of a significant difference between the bactericidal activity of T4 lysozyme and heat denatured T4 lysozyme. Heat-denatured T4 lysozyme, which no longer dissolves 100% under the selected conditions, shows no enzyme activity (muramidase). The mutant M6K, in which the 6th amino acid (methionine) has been substituted by lysine, exhibits higher bactericidal activity, since a hydrophobic amino acid has been replaced by a polar amino acid. The peptide A4, which includes amino needs 143–155 of the T4 lysozyme (in SEQ ID NO: 1), also shows no enzymatic muramidase activity, but has a significantly higher bactericidal activity.

Table 2 illustrates the fungicidal activity of the claimed invention using germinative zoospores of *Phytophthora nicotianae*.

TABLE 2

Relative length of germ tubes of *Phytophthora nicotianae* zoospores after 7 hrs. T4 lysozyme in 0.1 xPBS; heat-denatured T4 lys (10 min 80° C.) in 0.1 xPBS/1% DMSO; M6K mutant in 0.1 xPBS; peptide A4 in 0.1 xPBS (all final concentrations). The experiments were each carried out against blank controls with *P. nicotianae* containing the same volume of the relevant buffer, but no lysozyme or peptide.

| T4 lys in 0.1 xPBS 10 µg | Heat denatured T4 lys in 0.1 xPBS/1% DMSO 10 µg | M6K T4 lys mutant in 0.1 xPBS 10 µg | Peptide A4 in 0.1 xPBS 10 µg |
|---|---|---|---|
| 0.65 | 0.85 | 0.42 | 0.48 |

(Peptide A4 includes amino acids 143–155)

Fungus tests: Relative lengths of germ tubes

| T4 lys in buffer I 10 µg | Heat denatured T4 lys in buffer II 10 µg | M6K T4 lys mutant in buffer I 10 µg | Peptide A4 in buffer I 1 µg | Peptide A23 in buffer II 10 µg |
|---|---|---|---|---|
| 0.67 | 0.82 | 0.42 | 0.59 | 0.69 |

Peptide A23 includes AA 126–141 of T4 lysozyme
Buffer I: 20 µl buffer Al + 1 µl PBS
Buffer II: 20 µl buffer Al + 1 µl 50% DMSO/50% PBS
Buffer III: 20 µl buffer Al + 1 µl 40% DMSO/50% PBS, 0.3% Triton X-100

The polypeptides of the invention are useful as an additive to food (human or animal) or for other substances, to inhibit growth of microorganisms. The polypeptides may be applied to food indirectly by gerietically a food organism to express the polypeptides. The genetically modified plant is useful to prevent its own spoilage and/or as an additive to prevent the spoilage of other food components.

It will be appreciated by those of skill in the art that the antibiotic properties of the claimed polypeptides make them particularly suitable for use in therapeutic methods targeting such organisms.

A further field of application is in cancer therapy, since cancer cells have a similar cell membrane structure to bacterial cells, unlike the membranes of healthy eukaryotic cells, which have a quite different structure. In one embodiment, the polypeptides of the invention are screened for anti-cancer activity by a method comprising: (1) contacting malignant cells with the therapeutic polypeptide of the invention; (2) measuring the survival or proliferation of malignant cells; and (3) comparing the survival or proliferation of the cells contacted with the therapeutic polypeptide of the invention with the survival or proliferation of cells not so contacted (e.g., cells contacted with a control). A lower level of survival or proliferation in the contacted cells indicates that the preparation has anti-cancer activity. Examples of suitable cells are those which are derived from or display characteristics associated with a malignant disorder.

Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc.

Because of the ubiquitous occurrence of diseases caused by microorganisms, the polypeptides of the invention are numerous are useful in numerous fields of application. These uses range from human and veterinary medicine to resistance cultivation in plants and preventative use as bactericidal and fungicidal additives in foods. Furthermore, the properties of the polypeptides described herein are suitable for use in other fields of application, not connected with infection through microorganisms, e.g. in cancer therapy.

Another aspect of the present invention pertains to a method of controlling microbes, particularly pathogenic microbes, comprising applying to said microbes or applying to a microbe-inhabited locus an effective amount of an antibiotic polypeptide of the present invention.

The smaller partial sequences, which are preferably derived from the C-terminal part of T4 lysozyme, are particularly advantageous. For example, smaller peptides exhibit better penetration into the tissue, reduced allergenicity, higher antibiotic activity, and other advantages.

Compositions of the Invention

Amounts and locations for application of the antibiotic polypeptides and compositions of the present invention are generally determined by the target microbe and the site where the microbe is to be contacted with the antibiotic polypeptide (e.g., human or animal in vivo use, application to the surface of a plant, stored food, etc.), and the physical and functional (e.g., potency) characteristics of the specific polypeptide. Thus, it will be appreciated that a wide variety of compositions are possible within the scope of the invention.

Non-Pharmaceutical Antibiotic Compositions and Methods of Use

A wide variety of antibiotic compositions for non-pharmaceutical use are possible within the broad scope of the present invention. The antibiotic polypeptides may be encapsulated, included in a granular form, solubilized in water or other appropriate solvent, powdered, and included in any appropriate formulation for direct application to the situs of the target microbe.

The antibiotic polypeptides and their functional equivalents may be used either alone or in combination with other active or inactive substances and may be applied by any method known in the art including, for example, spraying, pouring, dipping, in the form of concentrated liquids, solutions, suspensions, sprays, powders, pellets and the like, formulated to deliver an antibiotically effective concentration of the antibiotic polypeptide. The antibiotic formulations may be applied in an antibiotically effective amount to an area of microbe infestation or an area susceptible to such infestation, e.g., a container of food, the surface of a plant, the soil in which a plant is growing or is intended to be grown, an animal, clothing, skin, and the like.

In all formulations described herein, materials which can lead to reduction in the antibiotic effectiveness of the polypeptides should be avoided but may be employed in appropriate circumstances where such materials do not entirely eliminate the antibiotic properties of the antibiotic polypeptide.

The antibiotic compositions may also include various antibiotically acceptable adjuvants known in the art. The term "adjuvant" is used herein to mean a substance added to a composition to aid the operation of the main ingredient. The adjuvants are antibiotically acceptable in that they do not completely diminish the antibiotic properties of the antibiotic polypeptide. Spray adjuvants are commonly employed in the application of agricultural chemicals. An effective spray adjuvant may be formulated to contain one or more surfactants, solvents or co-solvents.

Formulated antibiotic polypeptides can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other antibiotic additives, or surfactants. Liquid formulations may be aqueous-based or non-aqueous and employed as foams, gels, suspensions, emulsifiable concentrates, or the like. The ingredients may also include rheological agents, surfactants, emulsifiers, dispersants, or polymers.

The antibiotic polypeptides according to the instant invention can be utilized, in the form of the usual compositions or compositions with conventional inert (e.g., plant and/or animal compatible or herbicidally mammacidally inert) diluents or extenders, i.e. diluents, carriers or extenders of the type usable in conventional bactericidal or fungicidal compositions or compositions, e.g. conventional dispersible carrier vehicles such as gases, solutions, emulsions, suspensions, emulsifiable concentrates, spray powders, pastes, gels, soluble powders, dusting agents, granules, etc. These are prepared, for example, by extending the antibiotic polypeptides with conventional dispersible liquid diluent carriers and/or dispersible solid carriers optionally with the use of carrier vehicle assistants, e.g. conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.); halogenated, especially chlorinated, aromatic hydrocarbons (e.g. chlorobenzenes, etc.); cycloalkanes (e.g. cyclohexane, etc.); paraffins (e.g. petroleum or mineral oil fractions); chlorinated aliphatic hydrocarbons (e.g. methylene chloride, chloroethylenes, etc.); alcohols (e.g. methanol, ethanol, propanol, butanol, glycol, etc.), as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc. The antibiotic polypeptides may also be encapsulated in a liposomal composition (Belles et al in Pesticide Biochem. Physiol. 32, 1–10 (1988)). Esters, such as succinate ester or citrate esters, can be employed to control the buoyancy of the composition.

Another mechanism by which the antibiotic polypeptides can be made available to target microbes is through genetically engineering of organisms susceptible to infection by such microbes.

The antibiotic polypeptides of the present invention may be beneficially administered in conjunction with other active ingredients (sequentially or simultaneously), including pesticides, as well as various acaricides, algicides, antioxidants, anti-preservatives, bactericides, biocides, catalysts, chemical reactants, disinfectants, drugs, fermentation agents, fertility inhibitors, fertility promoters, fertilizers, food supplements, foods, fungicides, germicides, growth-regulating agents, herbicides, insecticides, microorganism attenuators, nematocides, plant growth inhibitors, plant growth promoters, preservatives, rodenticides, sex sterilants, and sterilization agents, and/or other agents that benefit the environment of use. For simultaneous administration, the active ingredients may be formulated into a unitary application form comprising at least one antibiotic polypeptide and one or more of such active ingredients.

Pharmaceutical Compositions and Methods of Use

The invention provides methods of treatment and prevention by administration to a subject in need of such treatment of a therapeutically or prophylactically effective amount of one or more antibiotic polypeptides of the invention. The subject is preferably an animal, including, but not limited to, animals such as monkeys, cows, pigs, horses, chickens, cats, dogs, etc., and is preferably a mammal, and most preferably human.

Various delivery systems are known and can be used to administer antibiotic polypeptides of the invention. For example, suitable systems include: encapsulation in liposomes, microparticles and/or microcapsules; recombinant cells capable of expressing the antibiotic polypeptide; receptor-mediated endocytosis; plasmids encoding one or more antibiotic polypeptides; viral vector delivery systems, etc. The antibiotic polypeptides can be delivered in a vesicle, in particular a liposome.

Methods of introduction include but are not limited to intradermal, intramuscular, intraperitoneal, intravenous, subcutaneous, intranasal, epidural, and/or oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection. An intraventricular catheter may be used to facilitate intraventricular injection, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment. For example, local administration may be achieved by topical application, by injection, by means of a catheter, by means of a suppository, or by means of an implant, the implant being of a porous, non-porous, or gelatinous material, including membranes, such as sialastic membranes, or fibers.

In yet another embodiment, the antibiotic polypeptide can be delivered in a controlled release system. A pump may be used as needed. Polymeric materials may also be employed in a controlled release system, according to methods known in the art. In yet another embodiment, a controlled release system can be placed in proximity of the therapeutic target, thus requiring only a fraction of the systemic dose.

In a specific embodiment a nucleic acid encoding one or more antibiotic polypeptides of the invention is administered by gene therapy methods as described herein, or as otherwise known in the art.

The pharmaceutical compositions comprise a therapeutically effective amount of one or more antibiotic polypeptides of the invention, and a pharmaceutically acceptable carrier.

The term "carrier" refers to a diluent, adjuvant, excipient, or vehicle with which the antibiotic polypeptide is administered to a subject. Examples of suitable pharmaceutical carriers are described in "Remington's Pharmaceutical Sciences" by E. W. Martin. Such compositions will contain a therapeutically effective amount of one or more antibiotic polypeptides of the invention, preferably in purified form, together with a suitable amount of carrier so as to provide the form for proper administration to the subject. The formulation should suit the mode of administration. In a preferred embodiment, the composition is formulated in accordance with routine procedures as a pharmaceutical composition adapted for intravenous administration to human beings. The compositions may also be formulated for veterinary use.

Examples of suitable pharmaceutical carriers include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Suppositories generally contain active ingredient in the range of 0.5% to 10% by weight; oral formulations preferably contain 10% to 95% active ingredient.

Oral formulation can include standard carriers such as pharmaceutical grades of mannitol, lactose, starch, magnesium stearate, sodium saccharine, cellulose, magnesium carbonate, etc.

Typically, compositions for intravenous administration are solutions in sterile isotonic aqueous buffer. Where necessary, the composition may also include a solubilizing agent and a local anesthetic such as lignocaine to ease pain at the site of the injection.

Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The antibiotic polypeptides of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the antibiotic polypeptide(s) and/or functional equivalent(s) of the invention that will be effective in the treatment of a particular disorder or condition depends on various factors and can readily be determined by one of skill in the art using standard clinical techniques with reference to the instant disclosure. For example, dosage amounts will depend on the nature of the disorder or condition. In vivo and/or in vitro assays may optionally be employed to help predict optimal dosage ranges. Effective doses may also be extrapolated from dose-response curves derived from vitro and in vivo experiments. Ranges will vary depending on the route of administration, the seriousness of the disease or disorder, the size of the subject, and other factors known in the art.

The invention also provides a pharmaceutical pack or kit comprising one or more containers filled with one or more of the ingredients of the pharmaceutical compositions of the invention. The kits preferably include instructions for administration of the composition. Optionally associated with such container(s) can be a notice in the form prescribed by a governmental agency regulating the manufacture, use or sale of pharmaceuticals or biological products, which notice reflects approval by the agency of manufacture, use or sale for human administration.

The invention is to be described in more detail, using the examples given below.

EXAMPLES

Production of Peptides and Proteins by Modification of the T4 Lysozyme

Starting from the purified T4 lysoyzme a mixture of peptide fragments are produced by digestion with suitable proteases (e.g. clostriapain, pepsin, trypsin). The mixture is separated into individual fragments using chromatographic methods (Reversed Phase HPLC with C 18 column).

The bactericidal effect of the individual fragments is readily determined by incubation (use of 1–10 µg polypeptide for a quantity of $1 \times 10^7$ bacteria cells) for one hour with *Escherichia coli* or other gram-negative (e.g. *Erwinia carotovora, Agrobacterium tumefaciens, Pseudomonas fluorescens*) or gram-positive type of bacteria (e.g. *Micrococcus lysodeikticus, Clavibacter michiganensis*), followed by plating out a dilution series of the suspension, and counting the surviving bacteria. The fungicidal effect of the individual fragments is determined by incubation for 20 hours with spores of *Phytophthora nicotianae*, or other fungus types, followed by plating out to determine the reduced growth length of the fungus hyphae. The activity is determined in relation to purified T4 lysozyme as standard.

Production of Peptides and Proteins by Chemical Synthesis

The antibiotic polypeptides of the invention may be produced by chemical synthsesis, described in more detail in Section 4.1. Partial sequences from the T4 lysozyme can also be chemically synthesized, e.g. the amphipathic alpha-helix 143–155. Determination of the bactericidal and fungicidal effects is carried out as described above.

Production of Peptides or Proteins Using Genetic Engineering

Starting from the coding DNA sequence for T4 lysozyme, or parts of this, certain sections of the DNA can be produced in the native state or with simultaneous introduction of modifications by means of methods for the production of recombinant DNA (see Sambrook et al., 1989, Molecular Cloning, A Laboratory Manual, Cold Spring Harbor Laboratory Press, New York), e.g. by new cloning of sub-fragments, by polymerase chain reaction amplification and modification or by site-directed mutagenesis. New DNA sequences for coding the polypeptides according to the invention can also be produced by chemical synthesis. The correctness of the DNA sequences generated in this way is checked by DNA sequencing. Thus the coding DNA sequences for the terminal-C half of the T4 lysozyme, from amino acid 74 up to amino acid 164, are cloned as a sub-fragment or for the amphipathic alpha-helix of the amino acids 143 to 155 are isolated by PCR amplification and cloned. Through site-directed mutagenesis the consensus sequence for N-glycosylation can be mutated in such a way that no more N-bound glycosylation takes place/e.g. Thr 142→Ala 142).

The recombinant genes produced are cloned under the control of suitable promoters, so that expression in the particular transgenic pro- or eukaryotic organism is possible. This process is described below using two examples.

Production in Bacteria with Subsequent Isolation

For expression of polypeptides, according to the invention in bacteria, the recombinant gene produced is cloned into a bacterial expression vector (e.g. from the pQE series, Qiagen). Simple purification of a so-called tag-peptide sequence, e.g. a 6×HIS tag, or a c-myc tag or a strep-tag, can be accomplished by fusing the nucleic acid sequence encoding the tag to the nucleic acid sequence encoding the polypeptide of the invention. Under the control of an inducible promotor (e.g. Tac promotor), exact biosynthesis of the polypeptides according to the invention can be carried out under controlled conditions. The polypeptide according to the invention is isolated and purified once using affinity chromatography over a nickel chelate column with the aid of the 6×HIS tag, giving a high purity product. Transmission into other prokaryotic organisms and biosynthesis of the polypeptides according to the invention in these takes place correspondingly.

Production of Transgenic Plants Without Isolation

For expression into transgenic eukaryotes the example of transgenic dicotyle plants has been selected. The recombinant genes, which code for the polypeptides according to the invention, are cloned under the control of promoters which are constitutive in plants, or regulatable active promoters (e.g. cauliflower mosaic virus 35S promotor, *Agrobacterium tumefaciens* Mannopin Synthase promotor, maize GapC4 promotor, potato Ubiquitin promotor). Furthermore, a terminator sequence is fused on 3' ends of the gene (e.g. Cauliflower mosaic virus 35S terminator, *Agrobacterium tumefaciens* Nopalin Synthase terminator, *Agrobacterium tumefaciens* Octopin Synthase terminator), in order to achieve stabilization of the transcribed mARNA.

The expression cassette is transferred into a binary vector (e.g. pBIN 19, pPCV701, pSR 8-30, pSR 8-35/1), which is suitable for the gene transfer by means of *Agrobacterium tumefaciens*. By infecting plant explants with these agrobacteria, which have been changed by genetic engineering, the gene is transferred into the plant. Transformation of plants can also be carried out with many other processes known in the art (e.g. with particle guns), apart from with *Agrobacterium tumefaciens*.

Introduction of exogenic genes into transgenic plants can be detected by suitable restriction digestion of the isolated genomic DNA, followed by Southern Hybridization, or by amplification of the exogenic DNA sequence can be accomplished with the aid of the polymerase chain reaction. Transcription of the genes into mRNA can be detected using the Northern Blot, or other suitable methods. Translation of the genes into the coded proteins can be examined and characterized using the Western Blot method, various constructed ELISA tests or other suitable methods. In this way the presence of polypeptides according to the invention can be proved.

Biological activity of the polypeptides is determined by the methods described earlier. Where the transformation is intended to produce a plant with resistance to a pathogen, the biological efficiency can also be determined by resistance tests on transgenic plants. The polypeptides of the invention can also be over-expressed in transgenic plants for production. Transmission into other eukaryotic organisms and biosynthesis of the polypeptides according to the invention therein takes place analogously.

One of skill in the art would understand that for optimum expression of the respective gene in individual eukaryotic organisms, it may be necessary to adapt the codons used to the preferred codons, and to adapt other factors which influence the stability of the mARNA and the polypeptide by methods known in the art.

Throughout this specification various patent and non-patent references have been cited. The entire disclosure of each such reference is incorporated herein by reference.

What is claimed is:

1. An antibiotic polypeptide comprising a modified T4 lysozyme, which exhibits antibiotic activity but which does not exhibit muramidase activity, wherein said antibiotic polypeptide consists of:
   (1) at least one fragment selected from the group consisting of:
      (a) amino acids 143–155 of SEQ ID NO: 1; and
      (b) amino acids 126–141 of SEQ ID NO: 1, with or without mutation at positions 140 and/or 141 of SEQ ID NO: 1; and
   (2) does not include the entire amino acid sequence SEQ ID NO: 1; and
   wherein the antibiotic polypeptide consists of
      (a) amino acids 12–164 of SEQ ID NO: 1;
      (b) amino acids 12–164 of SEQ ID NO: 1, with one or more mutations at any one or more of positions 140–142 of SEQ ID NO: 1;
      (c) amino acids 126–141 of SEQ ID NO: 1;
      (d) amino acids 126–141 of SEQ ID NO: 1, with one or more mutations at any one or more of positions 140–141 of SEQ ID NO: 1;
      (e) amino acids 143–155 of SEQ ID NO: 1;
      (f) amino acids 74–164 of SEQ ID NO: 1;
      (g) amino acids 74–164 of SEQ ID NO: 1, with one or more mutations at any one or more of positions 140–142 of SEQ ID NO: 1;
      (h) amino acids 114–164 of SEQ ID NO: 1;
      (i) amino acids 114–164 of SEQ ID NO: 1, with one or more mutations at any one or more of positions 140–142 of SEQ ID NO: 1; or
      (j) amino acids 124–164 of SEQ ID NO: 1.

2. The antibiotic polypeptide of claim 1, consisting of amino acids 12–164 of SEQ ID NO: 1, with one or more mutations at any one or more of positions 140–142 of SEQ ID NO: 1.

3. The antibiotic polypeptide of claim 1, consisting of amino acids 126–141 of SEQ ID NO: 1.

4. The antibiotic polypeptide of claim 1, consisting of amino acids 126–141 of SEQ ID NO: 1, with one or more mutations at any one or more of positions 140–141 of SEQ ID NO: 1.

5. The antibiotic polypeptide of claim 1, consisting of amino acids 143–155 of SEQ ID NO: 1.

6. The antibiotic polypeptide of claim 1, consisting of amino acids 74–164 of SEQ ID NO: 1.

7. The antibiotic polypeptide of claim 1, consisting of amino acids 74–164 of SEQ ID NO: 1, with one or more mutations at any one or more of positions 140–142 of SEQ ID NO: 1.

8. The antibiotic polypeptide of claim 1, consisting of amino acids 114–164 of SEQ ID NO: 1.

9. The antibiotic polypeptide of claim 1, consisting of amino acids 114–164 of SEQ ID NO: 1, with one or more mutations at any one or more of positions 140–142 if SEQ ID NO: 1.

10. The antibiotic polypeptide of claim 1, consisting of amino acids 124–164 of SEQ ID NO: 1.

* * * * *

UNITED STATES PATENT AND TRADEMARK OFFICE
CERTIFICATE OF CORRECTION

PATENT NO. : 6,515,106 B1
DATED : February 4, 2003
INVENTOR(S) : Klaus Düring

It is certified that error appears in the above-identified patent and that said Letters Patent is hereby corrected as shown below:

Column 2,
Line 65, "position s" should be -- positions --.

Column 6,
Line 37, "omithine" should be -- ornithine --.

Column 11,
Line 64, "gerietically" should be -- genetically --.

Column 18,
Line 41, "mARNA" should be -- mRNA --.

Column 20,
Line 2, "mARNA" should be -- mRNA --.

Signed and Sealed this

Twenty-second Day of July, 2003

JAMES E. ROGAN
*Director of the United States Patent and Trademark Office*

SEQUENCE LISTING

```
<160> NUMBER OF SEQ ID NOS: 4

<210> SEQ ID NO 1
<211> LENGTH: 164
<212> TYPE: PRT
<213> ORGANISM: Artificial Sequence
<220> FEATURE:
<223> OTHER INFORMATION: Mutated polypeptide formed by replacing the
      glutamic acid residue at position 11 of naturally-occurring
      lysozyme with some other amino acid.
<221> NAME/KEY: MISC_FEATURE
<222> LOCATION: (11)..(11)
<223> OTHER INFORMATION: X represents any amino acid except glutamic
      acid.

<400> SEQUENCE: 1

Met Asn Ile Phe Glu Met Leu Arg Ile Asp Xaa Arg Leu Arg Leu Lys
1               5                   10                  15
Ile Tyr Lys Asp Thr Glu Gly Tyr Tyr Thr Ile Gly Ile Gly His Leu
            20                  25                  30
Leu Thr Lys Ser Pro Ser Leu Asn Ala Ala Lys Ser Glu Leu Asp Lys
        35                  40                  45
Ala Ile Gly Arg Asn Cys Asn Gly Val Ile Thr Lys Asp Glu Ala Glu
    50                  55                  60
Lys Leu Phe Asn Gln Asp Val Asp Ala Ala Val Arg Gly Ile Leu Arg
65                  70                  75                  80
Asn Ala Lys Leu Lys Pro Val Tyr Asp Ser Leu Asp Ala Val Arg Arg
                85                  90                  95
Cys Ala Leu Ile Asn Met Val Phe Gln Met Gly Glu Thr Gly Val Ala
            100                 105                 110
Gly Phe Thr Asn Ser Leu Arg Met Leu Gln Gln Lys Arg Trp Asp Glu
        115                 120                 125
Ala Ala Val Asn Leu Ala Lys Ser Arg Trp Tyr Asn Gln Thr Pro Asn
    130                 135                 140
Arg Ala Lys Arg Val Ile Thr Thr Phe Arg Thr Gly Thr Trp Asp Ala
145                 150                 155                 160
Tyr Lys Asn Leu

<210> SEQ ID NO 2
<211> LENGTH: 17
<212> TYPE: PRT
<213> ORGANISM: Artificial Sequence
<220> FEATURE:
<223> OTHER INFORMATION: Mutated segments of Enterobacteria phage T4,
      comprising amino acids 126-141 and having the threonine at 141
      position replaced by another amino acid.
<221> NAME/KEY: MISC_FEATURE
<222> LOCATION: (17)..(17)
<223> OTHER INFORMATION: X represents any amino acid except threonine.

<400> SEQUENCE: 2

Trp Asp Glu Ala Ala Val Asn Leu Ala Lys Ser Arg Trp Tyr Asn Gln
1               5                   10                  15
Xaa

<210> SEQ ID NO 3
<211> LENGTH: 13
<212> TYPE: PRT
<213> ORGANISM: Artificial Sequence
<220> FEATURE:
<223> OTHER INFORMATION: Mutated segments of Enterobacteria phage T4,
      comprising amino acids 143-155 and having the threonine at 151
```

-continued

```
      position replaced by a phenylalanine.

<400> SEQUENCE: 3

Pro Asn Arg Ala Lys Arg Val Ile Phe Thr Phe Arg Thr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Artificial segment of Enterobacteria phage T4,
      comprising amino acids 126-140.

<400> SEQUENCE: 4

Trp Asp Glu Ala Ala Val Asn Leu Ala Lys Ser Arg Trp Tyr Asn Gln
1               5                   10                  15
```